United States Patent
Hsu

(10) Patent No.: US 9,572,521 B2
(45) Date of Patent: Feb. 21, 2017

(54) MONITORING BIOMETRIC CHARACTERISTICS OF A USER OF A USER MONITORING APPARATUS

(71) Applicant: George Hsu, Boca Raton, FL (US)

(72) Inventor: George Hsu, Boca Raton, FL (US)

(73) Assignee: PNI Sensor Corporation, Santa Rosa, CA (US)

( * ) Notice: Subject to any disclaimer, the term of this patent is extended or adjusted under 35 U.S.C. 154(b) by 316 days.

(21) Appl. No.: 14/022,390

(22) Filed: Sep. 10, 2013

(65) Prior Publication Data

US 2015/0073717 A1   Mar. 12, 2015

(51) Int. Cl.

| | |
|---|---|
| G01N 33/48 | (2006.01) |
| G01N 33/50 | (2006.01) |
| A61B 5/11 | (2006.01) |
| A61B 5/08 | (2006.01) |
| G06F 19/12 | (2011.01) |
| A61B 5/024 | (2006.01) |
| A61B 5/06 | (2006.01) |
| H01F 7/02 | (2006.01) |
| H01F 7/06 | (2006.01) |

(52) U.S. Cl.
CPC ......... *A61B 5/1121* (2013.01); *A61B 5/02438* (2013.01); *A61B 5/067* (2013.01); *A61B 5/0803* (2013.01); *G06F 19/12* (2013.01); *A61B 2562/0219* (2013.01); *A61B 2562/0223* (2013.01); *H01F 7/02* (2013.01); *H01F 7/06* (2013.01)

(58) Field of Classification Search
None
See application file for complete search history.

(56) References Cited

U.S. PATENT DOCUMENTS

| | | | | |
|---|---|---|---|---|
| 5,807,283 | A * | 9/1998 | Ng | A61B 5/11 600/595 |
| 2002/0188190 | A1* | 12/2002 | Kassai et al. | 600/410 |
| 2003/0083707 | A1* | 5/2003 | Yonce | 607/17 |
| 2010/0237858 | A1* | 9/2010 | Hokari | 324/244.1 |
| 2010/0245078 | A1 | 9/2010 | Nadkarni et al. | |
| 2012/0316455 | A1 | 12/2012 | Rahman et al. | |
| 2013/0077823 | A1 | 3/2013 | Mestha et al. | |
| 2013/0211291 | A1 | 8/2013 | Tran | |
| 2013/0231574 | A1 | 9/2013 | Tran | |
| 2013/0231711 | A1 | 9/2013 | Kaib | |

OTHER PUBLICATIONS

Clifton et al. Measurement of respiratory rate from the photoplethysmogram in chest clinic patients. Journal of Clinical Monitoring and Computing, 2006, seven pages.*

* cited by examiner

*Primary Examiner* — Russell S Negin
(74) *Attorney, Agent, or Firm* — Brian R. Short

(57) ABSTRACT

Apparatuses, methods and systems for a user monitoring apparatus are disclosed. One embodiment of the user monitoring apparatus includes one or more magnetic sensors operative to sense magnetic fields applied to the user monitoring apparatus. Further, the user monitoring apparatus is operative to sense at least one biometric characteristic of a user of the user monitoring apparatus based upon the sensed magnetic field applied to the user monitoring apparatus.

20 Claims, 7 Drawing Sheets

```
┌─────────────────────────────────────────────────────────────────────┐
│   Sensing, by one or more accelerometers, acceleration of a user monitoring device │
│                                                                     │
│                                 610                                 │
└─────────────────────────────────────────────────────────────────────┘
                                   ▼
┌─────────────────────────────────────────────────────────────────────┐
│  Sensing, by one or more magnetic sensors, magnetic fields applied to the user monitoring │
│                               device                                │
│                                                                     │
│                                 620                                 │
└─────────────────────────────────────────────────────────────────────┘
                                   ▼
┌─────────────────────────────────────────────────────────────────────┐
│      Sensing, by one or more gyroscopes, orientation of the user monitoring device │
│                                                                     │
│                                 630                                 │
└─────────────────────────────────────────────────────────────────────┘
                                   ▼
┌─────────────────────────────────────────────────────────────────────┐
│ Determining at least one biometric characteristic of the user of the user monitoring device │
│ based upon the sensed magnetic field applied to the user monitoring apparatus, and the sensed │
│                acceleration of the user monitoring device            │
│                                                                     │
│                                 640                                 │
└─────────────────────────────────────────────────────────────────────┘
                                   ▼
┌─────────────────────────────────────────────────────────────────────┐
│ Sensing orientation of the user based upon at least the sensed orientation of the user monitoring │
│                               device                                │
│                                                                     │
│                                 650                                 │
└─────────────────────────────────────────────────────────────────────┘
```

FIGURE 6

MONITORING BIOMETRIC CHARACTERISTICS OF A USER OF A USER MONITORING APPARATUS

FIELD OF THE EMBODIMENTS

The described embodiments relate generally to controlling a user monitoring apparatus. More particularly, the described embodiments relate to apparatuses, methods and systems for monitoring a biometric characteristic or a user orientation of a user of the user monitoring apparatus.

BACKGROUND

Current solutions for heart rate monitoring and respiration monitoring typically involve cumbersome and expensive equipment. For example, respiration and heart rate monitoring belts to be worn around the chest, spirometers and canulas to be worn around the mouth and nose, and electrocardiogram (ECG) electrodes and leads to be taped on the body. Not only are these solutions obtrusive and expensive, but may also be too restrictive to be well-suited for ambulatory monitoring.

Noise mixed with signals received by the sensors used in heart monitoring, respiration monitoring, body motion and other monitoring applications can adversely affect the accuracy of each type of signal. Accordingly, methods for robust detection and separation of such signals in noisy conditions are desirable. Accuracy of heart rate detection is important in many commercial heart monitoring applications (that is, heart rate monitors in exercise equipment, personal heart rate monitors) and medical heart monitoring applications (for example, digital stethoscopes, mobile cardiac monitoring devices).

It is desirable to have apparatuses, methods, and systems for more accurate and less cumbersome monitoring of one or more biometric characteristic of a user.

SUMMARY

An embodiment includes a user monitoring apparatus. The user monitoring apparatus includes one or more magnetic sensors operative to sense one or more magnetic fields applied to the user monitoring apparatus. Further, the user monitoring apparatus is operative to sense at least one biometric characteristic of a user of the user monitoring apparatus based upon the sensed one or more magnetic fields applied to the user monitoring apparatus.

Another embodiment includes a method of a user monitoring apparatus. The method includes sensing, by one or more accelerometers, acceleration of a user monitoring device, sensing, by one or more magnetic sensors, magnetic fields applied to the user monitoring device, sensing, by one or more gyroscopes, orientation of the user monitoring device, determining at least one biometric characteristic of the user of the user monitoring device based upon the sensed magnetic field applied to the user monitoring apparatus, and the sensed acceleration of the user monitoring device, and sensing orientation of the user based upon at least the sensed orientation of the user monitoring device.

Other aspects and advantages of the described embodiments will become apparent from the following detailed description, taken in conjunction with the accompanying drawings, illustrating by way of example the principles of the described embodiments.

BRIEF DESCRIPTION OF THE DRAWINGS

FIG. 6 is a flow chart that includes steps of a method of a user monitoring apparatus, according to an embodiment.

DETAILED DESCRIPTION

The described embodiments provide for apparatuses, methods, and systems for sensing a biometric characteristic of a user or an orientation of the user of a user monitoring apparatus. An embodiment of the user monitoring apparatus includes a magnetic sensor. An embodiment of the user monitoring apparatus includes a magnetic sensor and an accelerometer (or comparable motion sensor). An embodiment of the user monitoring apparatus includes a magnetic sensor and a gyroscope. An embodiment of the user monitoring apparatus includes a magnetic sensor, an accelerometer and a gyroscope. An embodiment includes a 9-axis fused system (3 gyroscope axis, 3 magnetic sensor axis, 3 accelerometer axis). For embodiments that include a plurality of sensors, a sensed signal of one of the sensors is used to correct or adaptively correct the sensed signal of another one of the plurality sensors.

At least some of the described embodiments of the user monitoring apparatus are used to detect at least one of breathing rate, amplitude, heart rate and subject position (lying down face up, face down, standing, which direction in compass heading the user (subject) is facing and limited dead reckoning positional movement), if the user monitoring apparatus is affixed, for example, to the chest of the user in a position in the proximity of the heart.

For an embodiment, a sensor fused output measures acceleration independent of orientation of the sensor module. The slight angular displacement of the sensor when the subject is breathing can be measured and represents the breath rate and breathing amplitude. The signals representing the breath rate and breathing amplitude can be signal processed out of the larger set of signals representing the subject's spatial position (standing, lying, etc.) or even amidst activity such as walking or running.

Sleep measurement, snoring, and apnea is an ideal application as the underlying activity represents a very benign signal conditioning exercise in order to extract the targeted measurement. The separate accelerometer-only measurement can extract the heart rate of the subject at the exact same location of the module, especially in reference to the fused sensor output as an input to a filter. The filtering techniques may consist of band pass filtering for the specific frequency spectra of interest given the targeted biometric measurement to be made, or application of more sophisticated signal extraction to increase accuracy and reject false signals when there is non-biometric signal of the same frequency spectra being cross coupled (i.e., running, sitting in a vehicle, etc.). This measurement device and approach could be used for sleep monitoring or elite athletic performance monitoring and can be used in both a consumer and clinical environment equally well.

Figure 1:
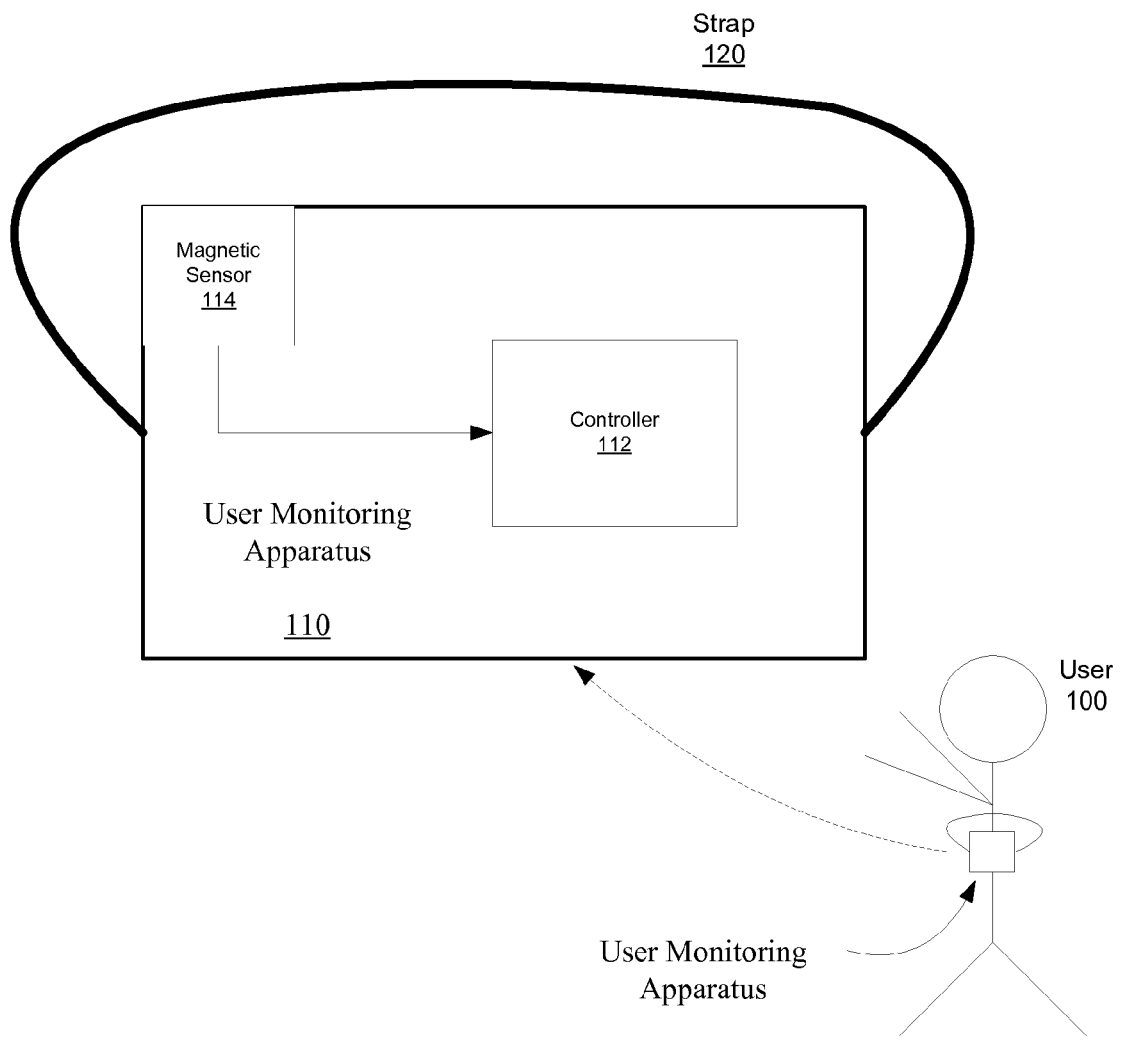
FIG. 1 shows a user monitoring apparatus that senses a biometric characteristic of a user or an orientation of the user of the user monitoring apparatus based upon the sensed magnetic field applied to the user monitoring apparatus, according to an embodiment.

FIG. 1 shows a user monitoring apparatus 110 that senses a biometric characteristic of a user 100 or an orientation of the user 100 of the user monitoring apparatus 110 based upon the sensed magnetic field applied to the user monitoring apparatus 110, according to an embodiment. As shown, the user monitoring apparatus 110 is affixed to the user 100. A strap 120 is shown that can be used to affix the user monitoring apparatus 110 to the user 100. However, other embodiments or methods of affixing the user monitoring apparatus 110 can be alternatively used.

For an embodiment, the user monitoring apparatus 110 includes a magnetic sensor 114. The user monitoring apparatus 110 further includes a controller 112 for processing sensed magnetic fields. For an embodiment, the magnetic sensor 114 includes one or more magnetic sensors operative to sense magnetic fields applied to the user monitoring apparatus 110. Further, the user monitoring apparatus 110 (or the controller 112) is operative to sense at least one biometric characteristic of a user of the user monitoring apparatus based upon the sensed magnetic field applied to the user monitoring apparatus.

For an embodiment, the at least one biometric characteristic includes a breathing characteristic of the user. For an embodiment, the at least one biometric characteristic includes a heartbeat characteristic of the user.

For an embodiment, the user monitoring apparatus is further operative to sense orientation of the user based upon at least one component of the sensed magnetic field applied to the user monitoring apparatus. For an embodiment, the at least one component of the sensed magnetic field includes a magnetic field of earth. For an embodiment, the at least one component of the sensed magnetic field includes a non-earth magnetic field of a magnetic source proximally located to the user monitoring apparatus.

For an exemplary specific embodiment, the permanent magnet provides a magnetic field of 10 gauss and the permanent magnet is located at a distance of approximately 2 inches from the sensor unit.

Figure 2:
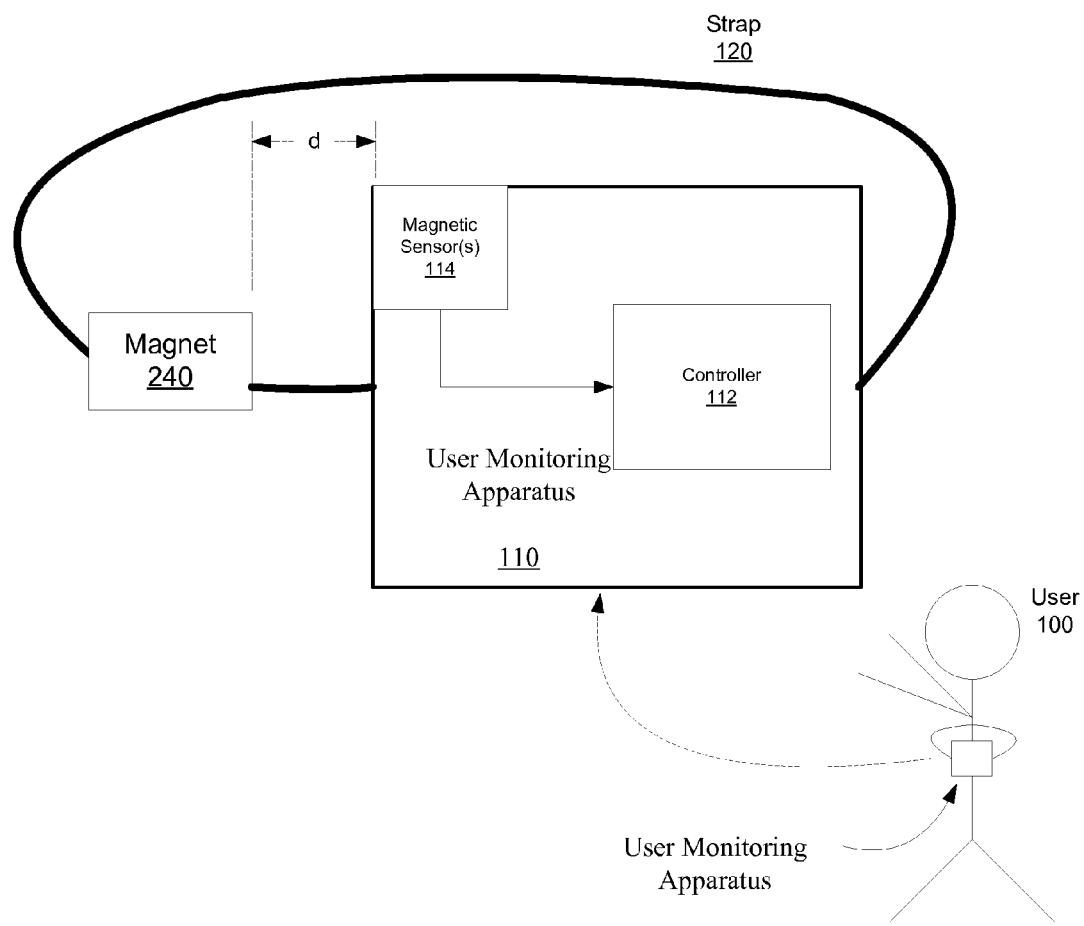
FIG. 2 shows a user monitoring apparatus that senses a biometric characteristic of a user or an orientation of the user of the user monitoring apparatus based upon the sensed magnetic field applied to the user monitoring apparatus, according to another embodiment.

FIG. 2 shows a user monitoring apparatus 110 that senses a biometric characteristic of a user 100 or an orientation of the user 100 of the user monitoring apparatus based upon the sensed magnetic field applied to the user monitoring apparatus 110, according to another embodiment. This embodiment further includes a magnetic source 240 that is proximally located near the user 100. For an embodiment, the magnetic source 240 proximally located to the user monitoring apparatus 110 includes a permanent magnet. For an embodiment, the magnetic source 240 proximally located to the user monitoring apparatus 110 includes a magnetic coil.

As described, one embodiment of the magnetic source includes a permanent magnet and another embodiment of the magnetic source includes a magnetic coil. Another embodiment of the magnetic source includes a combination of both a permanent magnet and a magnetic coil. For an embodiment, the level of the magnetic field of the magnetic source is selected to be strong enough to be detected by the magnetic sensor 111 but not so strong that the magnetic sensor 114 is saturated.

For an embodiment, the magnetic sensor 114 is mounted adjacent to the permanent magnet 240 (or electrical coil that can generate either an AC or DC magnetic field) to measure the intervening gap (the intervening gap having a gap distance "d" as shown in FIG. 2) between the magnet 240 and the magnetic sensor 114. The elastic band (strap 120) when affixed around the chest stretches and recovers between the maximum inhalation to the maximum exhalation chest circumferences and the intervening gap stretch displacements indicate the amount of air intake and rate of intake based upon the distance (gap distance d) between the magnet 240 and the magnetic sensor 114 at any given moment.

When the gap expands the field strength measured at the sensor decreases, while when the gap narrows the field expands. The relationship between the size of the gap and the magnetic field strength is typically not linear, but is given in the form of Gauss's equations. For an embodiment, a look up table is implemented to provide precise gap measurements based upon measured field strength. Generally, the relationship between the measured field strength and the gap is a $1/x^3$ function, and can be solved exactly if necessary. For an embodiment, field strength measurements are made at a maximum displacement and a minimum displacement of the gap. Further, fir at least some embodiments, an interpolation is performed to determine the magnetic field strength at points in between maximum displacement and a minimum displacement. As described, for at least some embodiments, the determined displacement of the gap is used to measure and/or monitor a biometric characteristic of the user 100.

It is to be understood that the elastic band is one embodiment which conveniently provides the characteristic of being elastic, which easily attaches to the user 100 aids in monitoring gap displacement. Another embodiment includes taping the user monitoring apparatus 110 (that includes the magnetic sensor 114) in place on, for example, the chest of the user, and further taping the magnet source one the user next to (proximate to) the user monitoring apparatus 110.

For an embodiment, this configuration measures both breathing rate as well as breathing volume for the subject (user 100) to be monitored and can also be used for both sleep monitoring or athletic activity or performance monitoring, especially in combination with the accelerometer based heart rate measurement. This particular measurement device has the added benefit of being immune to inertial effects, and so could form an additional baseline input to be a filter input parameter for the accelerometer based heart rate sensor.

An embodiment further includes a second magnetic sensor (attached, for example, to the strap 120) to allow for a gradiometer based measurement of the permanent magnet while rejecting ambient magnetic field influences (such as the earth's magnetic field, etc.).

For an embodiment, the second magnetic sensor is added and oriented in parallel to the axis of the first magnetic sensor, providing a 2 X's, 2 Y's, or 2 Z's sensed axis. At least some embodiments further include an entire set of 2 or 3 magnetic sensors in parallel, which are located some finite distance apart (say 5", although any distance could work). The multiple magnetic sensor embodiments provide or allow for common mode rejection of the sensed magnetic signals. Therefore, for example, the Earth's magnetic field, which is highly uniform, can simply be subtracted out by subtracting the reading of one sensor from another, the remaining signal being the signal of interest (the desired sensed magnetic signal).

For an embodiment, the magnet 240 is placed between the two magnetic sensors, or adjacent to either one. A small dipole of the magnet 240 is observed in the differential of the readings (sensed magnetic signals) between the two magnetic sensors, while any motion within the uniform earth magnetic field provides the same value on the both magnetic sensors. Therefore, the uniform earth magnetic field is canceled out when common mode rejection processing is applied to the sensed magnetic signals of the two magnetic sensors.

At least some embodiments further include sensing additional biometric readings that a full 9 axis system (3 motion sensor axis, 3 magnetic sensor axis, 3 gyroscope axis) can provide. For example, other possible biometric measurements include a wearers posture, gait and stride analysis, anxiety, sleep quality, etc. More specifically, the biometric measurements are not limited to breathing and heart rate.

Figure 3:
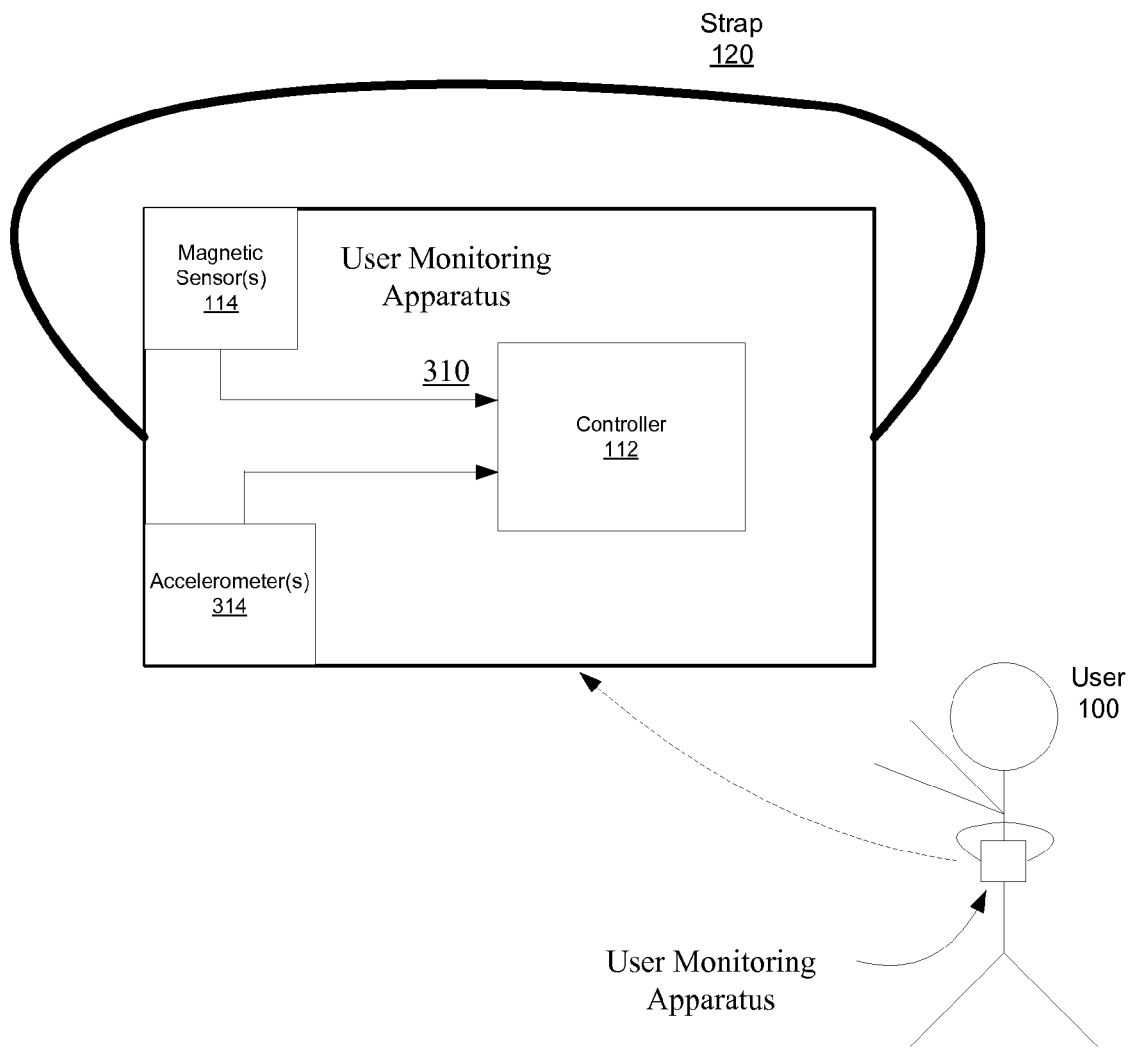
FIG. 3 shows a user monitoring apparatus that senses a biometric characteristic of a user or an orientation of the user of the user monitoring apparatus based upon the sensed magnetic field applied to the user monitoring apparatus and based upon sensed acceleration of the user monitoring apparatus, according to an embodiment.

FIG. 3 shows a user monitoring apparatus 310 that senses a biometric characteristic of a user 100 or an orientation of the user 100 of the user monitoring apparatus 310 based upon the sensed magnetic field applied to the user monitoring apparatus 310 and based upon sensed acceleration of the user monitoring apparatus 310, according to an embodiment. This embodiment includes the previously described magnetic sensor 114, and additionally includes a motion sensor (accelerometer 314). The addition of sensor allows for more accurate biometric sensing of the user, and can allow for sensing of additional biometric characteristics. The accelerometer is a second sensor that can measure motion which can be combined with what the magnetic sensor (s) measures.

For an embodiment, the motion sensor (accelerometer 314) includes one or more accelerometers operative to sense acceleration of the user monitoring apparatus. For an embodiment, the user monitoring apparatus 310 is further operative to sense the at least one biometric characteristic of the user 100 of the user monitoring apparatus 310 based upon the sensed acceleration of the user monitoring apparatus 310. For an embodiment, the at least one biometric characteristic includes a breathing characteristic of the user. For an embodiment, the at least one biometric characteristic includes a heartbeat characteristic of the user.

For at least some embodiments, the motion of the user sensed by the accelerometer(s) is used to cancel or minimize the effects of the user motion (as opposed to biometric motion) within the sensed magnetic signals. For at least some embodiments, the magnetic sensor 114 and the motion sensor 314 are utilized to measure motion, but measure the motion using different means. The varied structure of the magnetic sensor 114 and the motion sensor 314 provide different sensitivities and challenges to various aspects of motion. For instance, the accelerometer 314 is a small proof mass that responds to inertial motion. This subjects the accelerometer 314 to possible resonances of the proof mass structure that can result in high frequency signals overlaying on top of the signals of interest of the sensed motion signal. For at least some embodiments, the magnetic sensor 114 is used to correct for such false signals. Conversely, the magnetic sensor 114 is susceptible to transient magnetic fields in the user's environment, so if the sensed signal of the magnetic sensor 114 registers motion that is not biometrically generated, at least some embodiments include the accelerometer 314 providing an indication to the user monitoring apparatus 310 that the movement or signal was from an ambient noise source and not a signal of interest.

For an embodiment, the user monitoring apparatus is further operative to sense orientation of a user based upon at least one component of the sensed acceleration of the user monitoring apparatus.

For an embodiment, the at least one component of the sensed acceleration of the user monitoring apparatus includes a gravitational field of earth. Since the gravity vector is an acceleration vector, the orientation with respect to "down" that the accelerometer 314 measures is directly measured in G's. For at least some embodiments, the sensed acceleration of the accelerometer is integrated twice for determination of translational movements and a distance traversed by the user of the user monitoring apparatus 310.

Other sensors of the user monitoring apparatus can be used to compensate fir the user of low quality accelerometers. For example, in a fully fused 9-axis sensor system as will be described, the other sensors can supplement the sensed accelerometer signals, thereby allowing the use of lower quality accelerometers.

Figure 4:
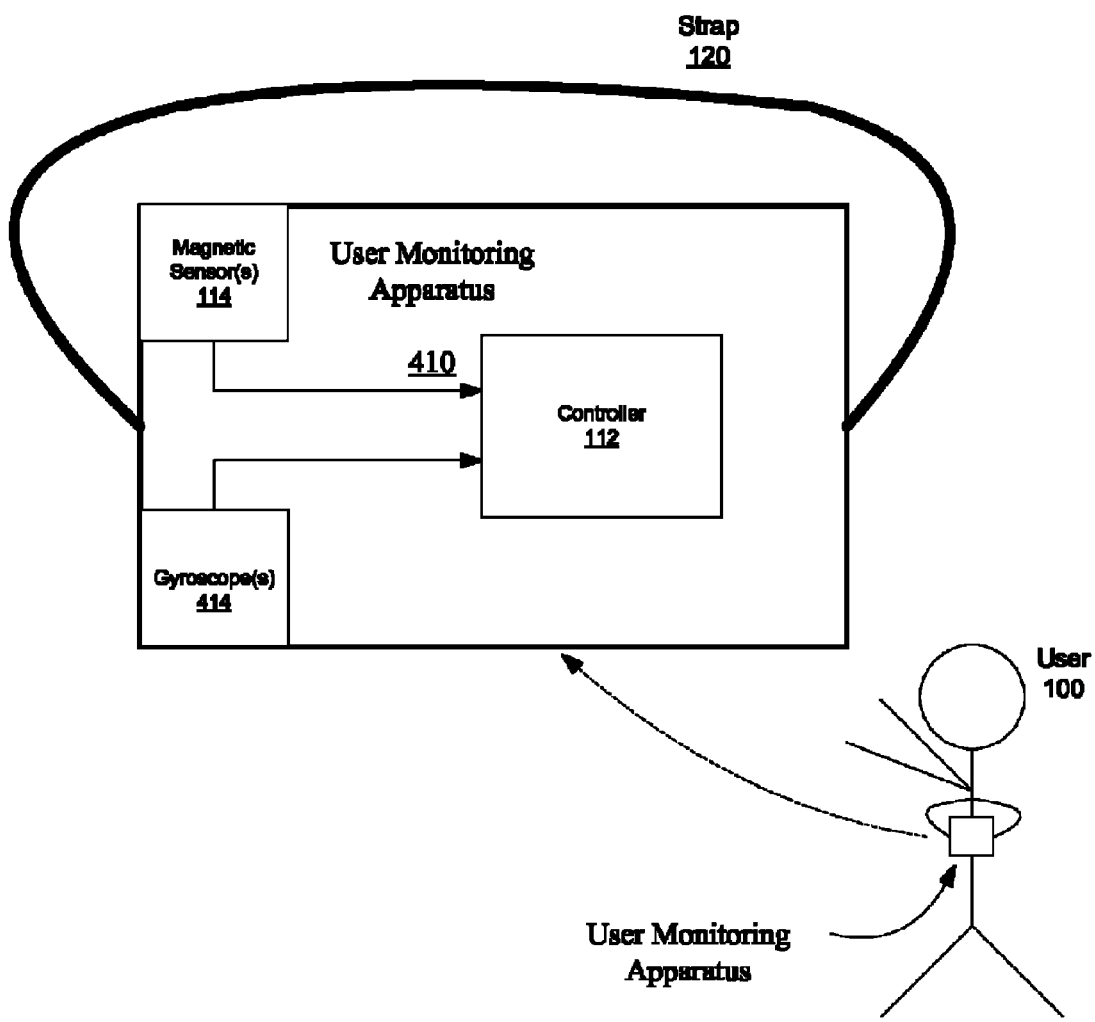
FIG. 4 shows a user monitoring apparatus that senses a biometric characteristic of a user or an orientation of the user of the user monitoring apparatus based upon the sensed magnetic field applied to the user monitoring apparatus and based upon sensed orientation of gyroscopes of the user monitoring apparatus, according to an embodiment.

FIG. 4 shows a user monitoring apparatus 410 that senses a biometric characteristic of a user 100 or an orientation of the user 100 of the user monitoring apparatus 410 based upon the sensed magnetic field applied to the user monitoring apparatus 410 and based upon sensed orientation of one or more gyroscopes 414 of the user monitoring apparatus 410, according to an embodiment.

A gyroscope is a device for measuring or maintaining orientation, based on the principles of angular momentum. Mechanically, a gyroscope is a spinning wheel or disc in which the axle is free to assume any orientation. Although this orientation does not remain fixed, it changes in response to an external torque much less and in a different direction than it would without the large angular momentum associated with the disc's high rate of spin and moment of inertia. Gyroscopes based on other operating principles also exist, such as the electronic, microchip-packaged MEMS gyroscope devices found in consumer electronic devices.

For an embodiment, the gyroscopes 414 include one or more gyroscopes operative to sense orientation of the user monitoring apparatus. For an embodiment, user monitoring apparatus is further operative to sense orientation of the user based upon at least the sensed orientation of the user monitoring apparatus. The one or more gyroscopes provide relative spatial orientation of the subject under measurement. When attached to a human body of a user, the gyroscopes can be used to measure the 3 dimensional rotational attitude of the body.

Figure 5:
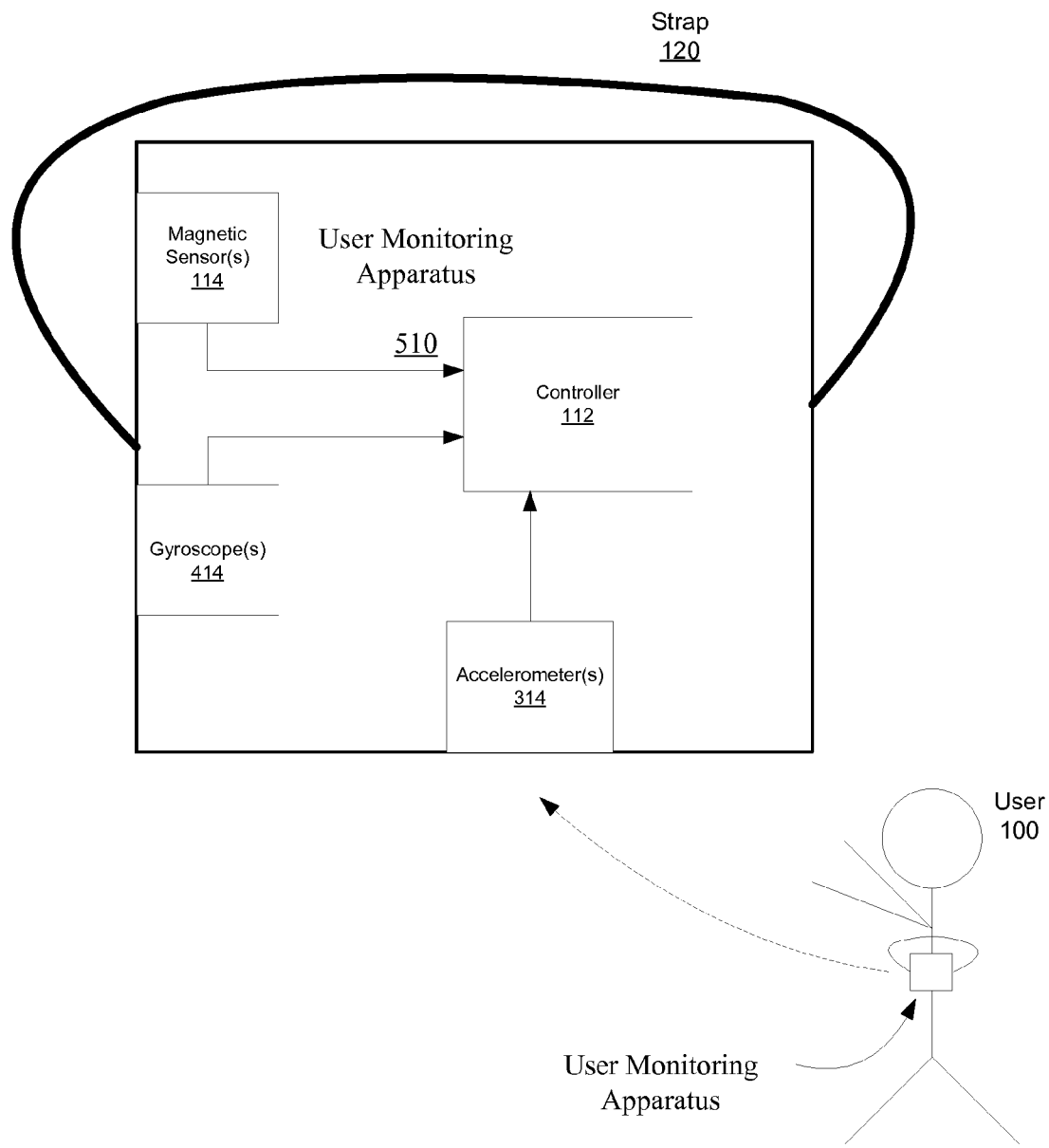
FIG. 5 shows a user monitoring apparatus that senses a biometric characteristic of a user or an orientation of the user of the user monitoring apparatus based upon the sensed magnetic field applied to the user monitoring apparatus, based upon sensed acceleration of the user monitoring apparatus, and based upon sensed orientation of gyroscopes of the user monitoring apparatus, according to an embodiment.

FIG. 5 shows a user monitoring apparatus 510 that senses a biometric characteristic of a user 100 or an orientation of the user 100 of the user monitoring apparatus 510 based upon the sensed magnetic field applied to the user monitoring apparatus 510, based upon sensed acceleration of the user monitoring apparatus 510, and based upon sensed orientation of gyroscopes 414 of the user monitoring apparatus 510, according to an embodiment. For an embodiment, the magnetic sensor 114 includes one or more magnetic sensors, the motion sensor (accelerometer 314) includes one or more accelerometers operative to sense acceleration of the user monitoring device, and the gyroscopes 414 include one or more gyroscopes operative to sense orientation of the user monitoring device. For an embodiment, the user monitoring device 510 is operative to sense the at least one biometric characteristic of the user 100 of the user monitoring apparatus 510 based upon the sensed magnetic field applied to the user monitoring apparatus 510, and the sensed acceleration of the user monitoring device 510, and sense orientation of the user 100 based upon at least the sensed orientation of the user monitoring device 510. For an embodiment, the at least one biometric characteristic of the user includes at least one of a breathing characteristic of the user, or a heartbeat characteristic of the user.

For an embodiment, the user monitoring device is further operative to sense velocity or spatial positioning of the user based upon at least the sensed orientation of the user monitoring device and a single or a double integration of the sensed acceleration of the user monitoring device. That is, integration of the sensed acceleration provides a representation of the velocity of the user, and a double integration of the sensed acceleration provides a representation of distance or spatial positioning of the user.

FIG. 6 is a flow chart that includes steps of a method of a user monitoring apparatus, according to an embodiment. A first step 610 includes sensing, by one or more accelerometers, acceleration of a user monitoring device. A second step 620 includes sensing, by one or more magnetic sensors, magnetic fields applied to the user monitoring device. A third step 630 includes sensing, by one or more gyroscopes, orientation of the user monitoring device. A fourth step 640 includes determining at least one biometric characteristic of the user of the user monitoring device based upon the sensed magnetic field applied to the user monitoring apparatus, and the sensed acceleration of the user monitoring device. A fifth step 650 includes sensing orientation of the user based upon at least the sensed orientation of the user monitoring device.

Figure 7:
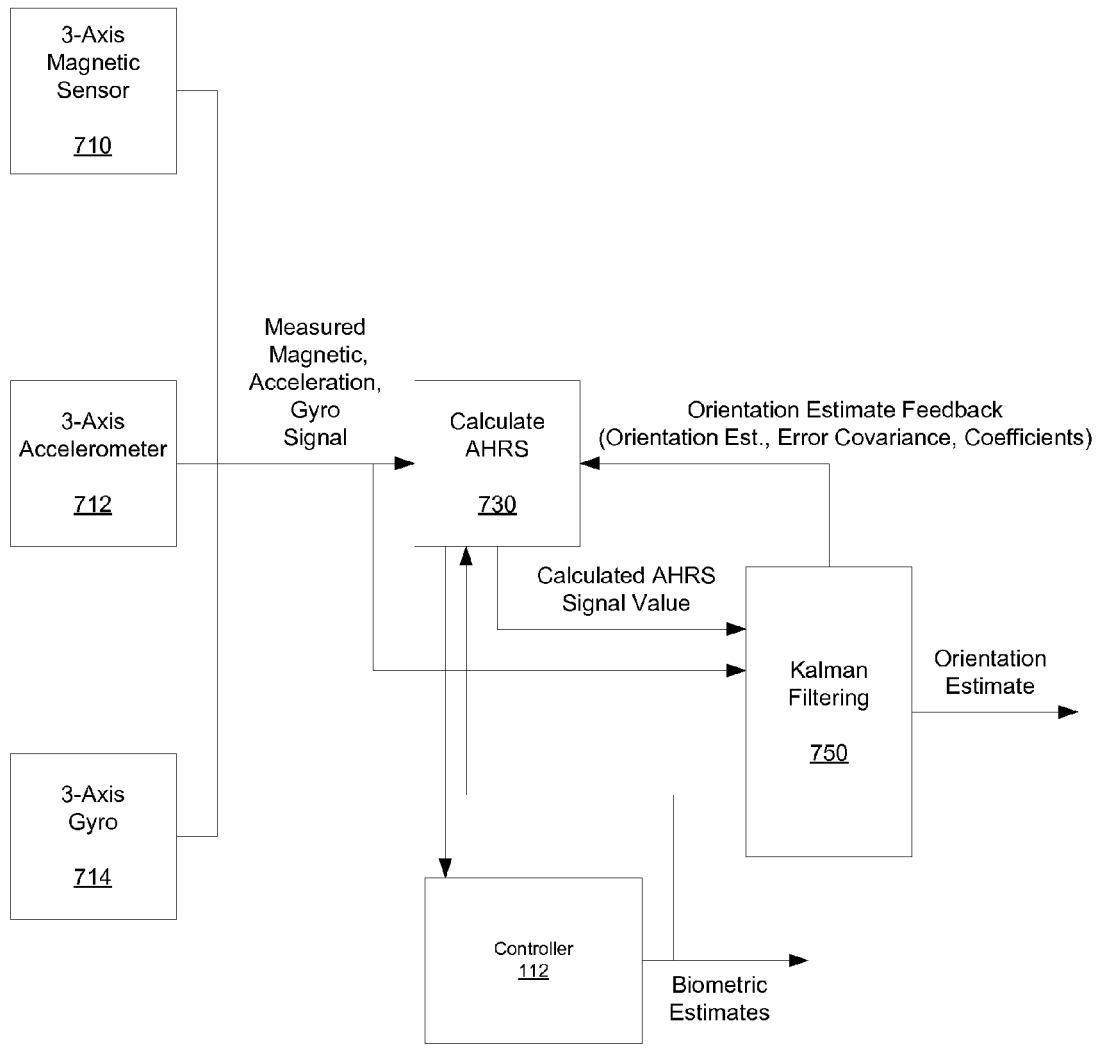
FIG. 7 shows a block diagram of an orientation module that the described embodiments are operable, according to an embodiment.

FIG. 7 shows a block diagram of an orientation module that the described embodiments are operable, according to an embodiment. An AHRS (attitude and heading reference system) sensor includes a 3-axis magnetic sensor 710, a 3-axis accelerometer 712 and a 3-axis gyro 714, references at least magnetic signals (for example, three orientations), resulting in a 9-axis AHRS system. The AHRS sensor senses acceleration (for example, three orientations which can include gravity), gyro signals (for example, three orientations) and magnetic signals (again, three orientations).

An AHRS calculation block 730 generates a calculated AHRS signal value based on the sensed AHRS signal, and feedback from a Kalman filter 750. The feedback can include orientation estimates including AHRS orientation estimates, error covariance and coefficients. The Kalman filter 750 yields an orientation estimate. For an embodiment, the attitude heading reference system (AHRS) consists of sensors on three axes that provide heading, pitch and roll information, for example, for an aircraft. The AHRS orientation modules were designed to replace traditional mechanical gyroscopic flight instruments and provide superior reliability and accuracy. However, the 9-axis AHRS can be used for other purposes, such as, orientation of a device or a user associated with the device.

Typically, the AHRS consist of either solid-state or MEMS gyroscopes, accelerometers and magnetometers on all three axes. In addition to attitude determination an AHRS may also form part of an INS (Inertial Navigation System). A form of non-linear estimation such as an extended Kalman filter is typically used to compute the solution from these multiple source. AHRS have proven themselves to be highly reliable and are in common use in commercial and business aircraft.

For at least some embodiments, an AHRS system is used to determine an orientation of a user. When used in association with a user, the biometric measurements are typically regarded as noise. As such, the biometric measurements of such systems are typically filtered out from the sensed signals.

FIG. 7 further includes the previously described controller 112, which receives 3-axis magnetic sensor information, 3-axis accelerometer information, and 3-axis gyro information from the AHRS calculation block 730. This embodiment allows for the use of poor quality sensors because each of the sensor types (magnetic, acceleration and gyro) can be used to supplement the poor or low-grade performance provided by each of the sensor types individually. For example, motion of the user can influence the sensed biometric measurements made by a particular sensor. User motion of another type of the sensors can be used to cancel the user motion from the sensed biometric signal of the particular sensor.

For example, an embodiment includes utilizing adaptive filtering. More specifically, an embodiment includes at least a plurality of sensors (for example, magnetic sensor, accelerometer, and gyro) wherein each of the sensors suffers from poor noise performance, but because noise of each of the sensors is distinct from each other, there is a way to combine them (adaptively filter and combine) by using probabilities to figure out the actual underlying truth or condition of the user. For instance, an accelerometer is sensitive to linear vibratory noise, but a gyro is not. However, a gyro has long term bias drift that causes integration error to result in large accumulated angular offsets. However, the long term accuracy of an accelerometer is good in determining which direction down is, so the adaptive filter can figure out when the gyro can have its bias error corrected for by the accelerometer. For the embodiments described here, the accelerometer might be measuring linear acceleration of high frequency (relatively speaking), which is the heart rate. Normally, this is not a desired signal and would be considered noise that the adaptive filter would reject in using to correct for the long term gyro bias drift. However, for the described embodiments, the accelerometer measurement and can be use it to determine heart rate, but the gyro output can be used to subtract out any offset that gravity might inject into this heart rate measurement by the accelerometers.

More specifically, an embodiment includes a user monitoring apparatus, wherein the user monitoring apparatus includes a magnetic sensor, accelerometer, and gyro. Further, the user monitoring apparatus includes a controller 112, wherein the controller 112 is operative to sense at least one biometric characteristic of a user of the user monitoring apparatus based upon a sensed acceleration and a sensed magnetic field applied to the user monitoring apparatus, and monitor orientation based on the sensed gyro signal. More specifically, the accelerometer provides a sensed heart rate of the user, and the accelerometer provides a bias signal for correcting a bias error of a sensed gyro signal. Further, the gyro signal provides the orientation of the user, and provides an offset signal which is used to correct a gravity offset signal present in the sensed acceleration signal.

Sensing of biometric signals by the controller 112 can be used to advantageously provide cancellation of these signals from the orientation estimations, along with providing the biometric signal determinations. That is, the interference within the orientation signals caused by the sensed biometric signals is canceled while still using the biometric signals for providing biometric information about the user.

Although specific embodiments have been described and illustrated, the described embodiments are not to be limited to the specific forms or arrangements of parts so described and illustrated. The embodiments are limited only by the appended claims.

What is claimed:

1. A user monitoring apparatus, comprising:
a first magnetic sensor operative to sense a first magnetic field applied to the user monitoring apparatus and a second magnetic sensor operative to sense a second magnetic field applied to the user monitoring apparatus, wherein the second magnetic sensor is oriented in parallel with an axis of the first magnetic sensor;
a magnetic source, wherein the magnetic source is located proximate to the first and second magnetic sensors forming a gap between the magnetic source and the first and second magnetic sensors; wherein
the user monitoring apparatus is operative to:
sense at least a rate of breathing and amounts of air intake of a user of the user monitoring apparatus based upon a sensed rate of displacement and a sensed amount of displacement of the gap as determined by a difference between the sensed first magnetic field and the sensed second magnetic field, wherein the sensed displacement of the gap indicates a change in a distance between the magnetic source and the first and second magnetic sensors.

2. The apparatus of claim 1, wherein the user the user monitoring apparatus further comprises an elastic strap, wherein the elastic strap is configured to be attached about a chest of the user, and wherein the elastic strap is configured to stretch to maximum inhalation chest circumference of the user and recover to maximum chest exhalation of the user.

3. The apparatus of claim 1, wherein the user monitoring apparatus is further operative to sense a heartbeat characteristic of the user.

4. The apparatus of claim 1, wherein the user monitoring apparatus is further operative to:
sense orientation of the user based upon at least one component of the sensed magnetic field applied to the user monitoring apparatus.

5. The apparatus of claim 4, wherein at least one component of the sensed magnetic fields includes a magnetic field of earth.

6. The apparatus of claim 4, wherein at least one component of the sensed magnetic fields includes a non-earth magnetic field of the magnetic source proximally located to the user monitoring apparatus.

7. The apparatus of claim 6, wherein the magnetic source proximally located to the user monitoring apparatus includes a permanent magnet.

8. The apparatus of claim 6, wherein the magnetic source proximally located to the user monitoring apparatus includes a magnetic coil.

9. The apparatus of claim 1, further comprising one or more accelerometers operative to sense acceleration of the user monitoring apparatus.

10. The apparatus of claim 9, wherein the user monitoring apparatus is further operative to sense at least one biometric characteristic of the user of the user monitoring apparatus based upon the sensed acceleration of the user monitoring apparatus.

11. The apparatus of claim 10, wherein the at least one biometric characteristic includes a breathing characteristic of the user.

12. The apparatus of claim 10, wherein the at least one biometric characteristic includes a heartbeat characteristic of the user.

13. The apparatus of claim 10, wherein the user monitoring apparatus is further operative to sense orientation of a user based upon at least one component of the sensed acceleration of the user monitoring apparatus.

14. The apparatus of claim 13, wherein the at least one component of the sensed acceleration of the user monitoring apparatus includes a gravitational field of earth.

15. The apparatus of claim 1, further comprising one or more gyroscopes operative to sense orientation of the user monitoring apparatus.

16. The apparatus of claim 15, wherein user monitoring apparatus is further operative to sense orientation of the user based upon at least the sensed orientation of the user monitoring apparatus.

17. The apparatus of claim 1, wherein user monitoring apparatus further comprises:
one or more accelerometers operative to sense acceleration of the user monitoring device;
one or more gyroscopes operative to sense orientation of the user monitoring device; wherein
the user monitoring device is operative to:
sense at least one biometric characteristic of a user of the user monitoring apparatus based upon the sensed first and second magnetic fields applied to the user monitoring apparatus, and the sensed acceleration of the user monitoring device; and
sense orientation of the user based upon at least the sensed orientation of the user monitoring device.

18. The apparatus of claim 17, wherein the at least one biometric characteristic of the user includes at least one of a breathing characteristic of the user, or a heartbeat characteristic of the user.

19. The apparatus of claim 17, wherein the user monitoring device is further operative to sense velocity or spatial positioning of the user based upon at least the sensed orientation of the user monitoring device and a single or a double integration of the sensed acceleration of the user monitoring device.

20. A method of monitoring a user, comprising:
sensing, by one or more accelerometers, acceleration of a user monitoring device;
sensing, by first and second magnetic sensors, first and second magnetic fields applied to the user monitoring device, wherein at least a portion of the sensed magnetic fields are from a magnetic source, wherein the magnetic source is located proximate to the one or more magnetic sensors forming a gap between the magnetic source and at least one of the one or more magnetic sensors;
sensing, by one or more gyroscopes, orientation of the user monitoring device;
determining a breathing rate and amounts of air intake of the user of the user monitoring device based upon a sensed rate of displacement and a sensed amount of displacement of the gap as determined by a difference between the sensed first and second magnetic fields, and the sensed acceleration of the user monitoring device, wherein the sensed displacement of the gap indicates a change in a distance between the magnetic source and the first and second magnetic sensors; and sensing orientation of the user based upon at least the sensed orientation of the user monitoring device.

* * * * *